United States Patent [19]

Slocum

[11] Patent Number: 4,565,191

[45] Date of Patent: Jan. 21, 1986

[54] APPARATUS AND METHOD FOR PERFORMING CUNEIFORM OSTEOTOMY

[76] Inventor: D. Barclay Slocum, 241 Spy Glass Dr., Eugene, Oreg. 97401

[21] Appl. No.: 570,458

[22] Filed: Jan. 12, 1984

[51] Int. Cl.⁴ .............................................. A61F 5/04

[52] U.S. Cl. ............................ 128/92 H; 128/92 EB; 128/92 D

[58] Field of Search ............ 128/92 H, 92 EB, 92 D, 128/92 E, 303 R, 92 A

[56] References Cited

U.S. PATENT DOCUMENTS

| | | | |
|---|---|---|---|
| 4,150,675 | 4/1979 | Comparetto | 128/92 E |
| 4,349,058 | 9/1982 | Comparetto | 128/92 E |
| 4,433,681 | 2/1984 | Comparetto | 128/92 R |
| 4,501,268 | 2/1985 | Comparetto | 128/92 H |
| 4,502,474 | 3/1985 | Comparetto | 128/92 E |
| 4,502,483 | 3/1985 | Lacey | 128/92 H |
| 4,509,511 | 4/1985 | Neufeld | 128/92 H |

*Primary Examiner*—Gene Mancene
*Assistant Examiner*—C. W. Shedd
*Attorney, Agent, or Firm*—Kolisch, Hartwell & Dickinson

[57] ABSTRACT

An apparatus and method for performing a cuneiform osteotomy as provided, the apparatus including a drill jig and an osteotomy guide. The jig has first and second faces which terminate in edges and which define a recess extending therethrough and intersecting an edge thereof, the jig further defining a pair of jig bores extending therethrough in a direction substantially perpendicular to the first jig face, one of each of the jig bores being disposed to each side of the recess. The jig bores are each adapted to properly position a drill bit extending therethrough and into the bone against which the second jig face is adapted to be disposed and to which the osteotomy is being performed. The osteotomy guide has first and second substantially parallel faces which complement the first jig face and which terminate in lateral edges. The guide defines a pair of guide bores extending therethrough in a direction substantially perpendicular to the guide faces, the guide bores being spaced from each other a distance equal to the spacing of the jig bores. Therefore, each of the guide bores is adapted to receive one of the drill bits to permit relative alignment of the jig and guide with respect to each other and the bone. The guide further defines a slot extending therethrough across less than the entire width of the guide and intersecting an edge thereof. The slot extends at an oblique angle with respect to a line drawn between the jig bores. Thus, the guide may be mounted to the jig with either of the guide faces disposed against the first jig face permitting the guide slot to be disposed in a first and then in a second angular position with respect to the bone. This facilitates cutting the bone in first and second cuts to excise a bone wedge of an angle alpha which is equal to the difference between the first and second angular positions of the slot.

13 Claims, 8 Drawing Figures

APPARATUS AND METHOD FOR PERFORMING CUNEIFORM OSTEOTOMY

BACKGROUND OF THE INVENTION

The invention relates generally to osteotomy techniques and more particularly to an apparatus and method for performing cuneiform osteotomy.

Various techniques have been developed over the years for performing cuneiform osteotomy; that is, surgical removal of a bone wedge such as from a leg bone to correct impairments to the bone, the musculature or the ligamental support associated therewith.

The cranial or anterior cruciate ligament restrains cranial drawer or sliding motion of the tibia of a dog. When the cranial cruciate ligament is disrupted or injured, the tibia moves interiorly with respect to the femur, leading to further injury of the musculature, ligaments or meniscus. A wide variety of methods of repairing the cranial cruciate ligament have been suggested ranging from collagen ligament implants to synthetic ligament implants. Extra-articular repair devices have also been proposed, but none of these has been successful. Collagen implants stretch with use, leaving the knee area unstable, while synthetic implants are unable to withstand the varied forces exerted on the knee. Extra-articular repairs decrease mobility and place undue stress on the soft tissue surrounding the joint which is not designed for constant loads.

It has been recognized that one problem with most techniques for repairing a dog's cranial cruciate ligament is that the phenomenon of cranial tibial thrust has not been appreciated. This phenomenon results from the natural slope of the tibial plateau which results in force factors having compressive and cranial or anterior components. The compressive components are satisfactorily absorbed by the tibia, as are the cranial tibial forces when the cranial cruciate ligament is operating satisfactorily. When the cranial cruciate ligament is weakened by injury or is congenitally malformed, cranial tibial thrust can be a problem. Many prior efforts at repair of a weakened cranial cruciate ligament ignore the cranial tibial thrust phenomenon and have failed to recognize that this phenomenon results in the ligament being placed under stress while healing was intended to occur. Such stress clearly retards or prevents any such healing.

Once cranial cruciate rupture occurs, so-called cranial drawer or sliding motion, that is, unrestrained motion of the tibia following such rupture, results in more severe injury to the dog's leg. Surgical attempts have been addressed to restraining cranial draw motion but, until recently, no attempt has been made to deal with internally generated cranial tibial thrust.

The cranial tibial cuneiform osteotomy was developed to address the cranial tibial thrust phenomenon. It involves removing a wedge from the distal third of the tibia, and rejoining the bone using an osteopathic compression plate. This technique flattens the tibial plane and thereby eliminates cranial tibial thrust, permitting the cranial cruciate ligament to heal normally in a nonstressed condition.

While the cranial tibial cuneiform osteotomy has provided a solution to the afore-described problems, the operation itself has, until now, been somewhat cumbersome. It has required a substantial amount of skill in order to remove an appropriate wedge of bone which would flatten the tibial plane. The positioning of the drill holes by which the osteopathic compression plate has been mounted is also critical and has presented another technical problem with the operation. The operation has been further complicated by the fact that means has not been provided for supporting the osteopathic saw during the cutting of the bone. Even for the most skilled surgeon, this lack of support can and often does present difficulties. This is an operation which is performed regularly but typically not on a daily basis so that any device developed to faciliate the operation should be low in cost, relatively small due to storage space limitations, and should be easy to use by an veterinary surgeon who may not perform the operation on a regular basis.

It is an object of the present invention to provide an apparatus and method which meets the afore-described problems. More specifically, the invention has as its objects the following:

(1) to provide a surgical technique which eliminates cranial tibial thrust forces and thereby causes forces on the tibia to be compressive rather than angular, facilitating proper healing of the associated muscles and ligaments;

(2) to provide a device which fac:litates cranial tibial cuneiform osteotomy by a veterinary surgeon who does not have an opportunity to perform such operations on a regular basis;

(3) the provision of a device useable in cuneiform osteotomies which is simple in structure, inexpensive, physically small, and which will be long-lasting;

(4) to develop an apparatus for performing a cuneiform osteotomy which facilitates the precise positioning of osteopathic compression plate holes and which predetermines the exact amount and shape of bone to be removed; and (5) to provide an apparatus and method for performing a cuneiform osteotomy in which the osteopathic saw is supported and precisely positioned without the use of intricate, expensive equipment, or a high degree of skill on the part of the surgeon.

SUMMARY OF THE INVENTION

The above objects are best achieved by providing an apparatus for performing cuneiform osteotomy which includes a jig and an osteotomy guide. The jig hs first and second faces which terminate in edges and which define a recess extending therethrough and intersecting an edge thereof. The jig further defines a pair of jig bores extending therethrough in a direction substantially perpendicular to the first jig face, one of each of the jig bores being dispsoed to each side of the recess, the jig bores each being adapted to properly position a drill bit extending therethrough and into the bone against which the second jig face is adapted to be dispsoed and to which the osteotomy is being performed.

The osteotomy guide has first and second substantially parallel faces which complement the first jig face and which terminate in lateral edges. The guide defines as pair of guide bores extending therethrough in a direction substantially perpendicular to the guide faces, the guide bores being spaced from each other a distance equal to the spacing of the jig bores. Therefore, each of the guide bores is adapted to reeive one of the drill bits to permit relative alignment of the jig and the guide with respect to each other and the bone. The guide further defines a slot extending therethrough across less than the entire width of the guide and intersecting an edge thereof. The slot extends at an oblique angle with respect to a line drawn between the guide bores. Thus, the guide may be mounted to the jig with either of the guide fces disposed against the first jig face, permitting the guide slot to be disposed in a first and then in a second angular position with respect to the bone. This facilitates cutting the bone in first and second cuts to excise a bone wedge of an angle alpha which is equal to the difference between the first and second angular positions of the slot.

Another aspect of the invention is a method of performing a cranial tibial cuneiform osteotomy using the aforedescribed apparatus. Specifically, the method comprises the steps of (1) placing the jig on the exposed medial side of the tibia, (2) drilling aproximal hole in the tibia with a drill passing through one of the proximally-disposed jig bores, and leaving the drill bit in place, (3) drilling a distal hole in the tibia with a drill bit passing through one of the distally-disposed jig bores, and leaving the drill bit in place, (4) drilling additional holes in the tibia with a drill bit passing through the jig's remaining bores, then removing that drill bit, (5) placing, over the jig, the osteotomy guide so that the previously-placed drill bits extend through the guide bores and position the first guide face against the first jig face, (6) making a first osteotomy cut in the tibia with an osteotomy saw extending through the guide slot, (7) turning the guide end over end and placing the second guide face against the first jig face, with the guide bores receiving the previously-placed drill bits, (8) making a second osteotomy cut in the tibia with an osteotomy saw extending through the guide slot, (9) removing the guide, jig and drill bits, (10) removing the bone portion excised by the cuts, and (11) drawing together and securing the separted portions of the tibia with interfragmentary compression. The interfragmentary compression is normally applied by placing a compression plate adjacent the first and second osteotomy cuts, and securing the compression plate to the tibia with screws extending into the holes previously drilled in the tibia.

These and other advantages and features of the present invention will become apparent when consideration is given to the following detailed description and the accompanying drawings.

DETAILED DESCRIPTION OF THE INVENTION

Construction of the Depicted Embodiment

Figure 3:
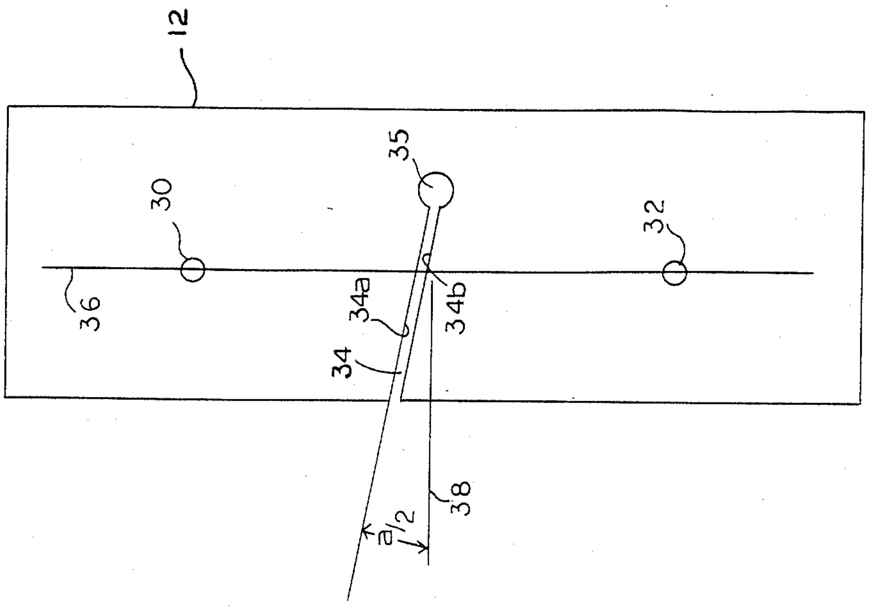
FIG. 3. Is a plan view of the embodiment of the osteotomy guide depicted in FIGS. 1, 2.
Figure 2:
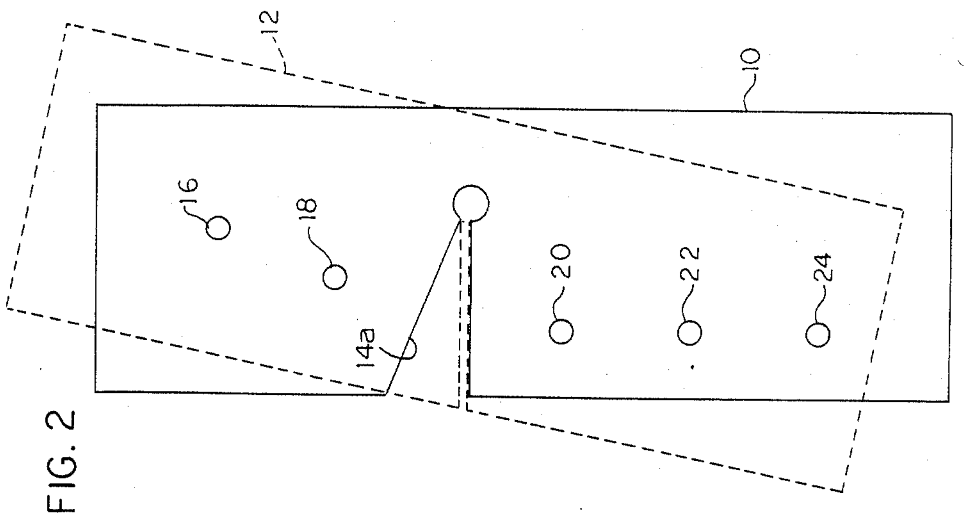
FIG. 2. Is a plan view corresponding that of FIG. 1, except that the osteotomy guide is shown in a second angular position.
Figure 1:
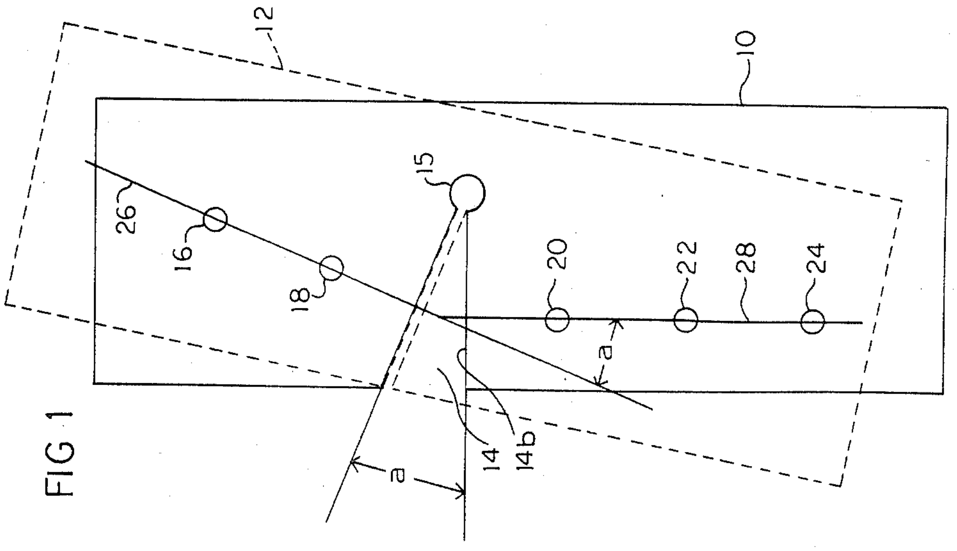
FIG. 1 is a plan view of a first embodiment of drill jig used as a part of the invention, with an embodiment of an osteotomy guide depicted in phantom in a first angular position above the drill jig.

The objects of the present invention are particularly well-achieved when the invention takes the form of the apparatus depicted in the figures The apparatus includes a drill jig 10, and an osteotomy guide 12, the construction of these members being shown best in FIGS. 1–3. Making reference to FIGS. 1 and 2, it can been seen that the major planar surface of drill jig 10 is rectangular in configuration, and includes a wedge-shaped recess 14 defined along one of its major edges. Recess 14 extends across a major portion of the width of drill jig 10 and terminates in a drill aperture 15, the purpose of which will be described below. As shown in FIG. 1, recess 14 subtends an angle alpha (a) for purposes which will become evident as this description continues.

Drill jig 10 also includes a plurality of drilled holes or bores, such bores being identified with numerals 16, 18, 20, 22, and 24. Holes 16 and 18 are disposed on the so-called proximal side of recess 14, while bores 20, 22, 24 are disposed on the so-called distal side. Bores 16 and 18 extend at an angle with respect to the lateral edges of drill jig 10 along an imaginary line which has been indicated at 26 in FIG. 1. Bores 20, 22, 24, are preferably aligned parallel to the major or lateral edges of drill jig 10 along an imaginary line 28. As shown in FIG. 1, lines 26 and 28 also intersect at the alpha (a) angle.

Bores 16, 18, 20, 22, and 24 are typically approximately 0.08 inches in diameter, although this size may be varied depending upon the particular application. Drill jig 10 itself is normally three inches in length, one inch wide and approximately 0.3 inches thick if the jig is being used for cranial tibial cuneiform osteotomy on a dog, but the size may vary depending upon the particular application. Of course, if the apparatus is being used to perform some other type of cuneiform osteotomy, its size vary substantially from that suggested. Angle alpha (a) is normally approximately 22.5°, as this angle has been found to be suitable for most cranial cuneiform osteotomies performed on dogs. Of course, if the operation is being used for any other purpose, the angle might be substantially different.

Osteotomy guide 12 is shown best in FIG. 3. It also is preferably rectangular in configuration, and includes a pair of holes or bores 30, 32, and an angular slot 34 extending outwardly across a substantial portion of its width, to one of its major or lateral edges. The spacing between guide bores 30 and 32 is normally identical to that of bores 16, 18, 20, 22, and 24, that is, approximately 0.08 inches. Guide bores 30 and 32 are shown to be aligned along an imaginary line 36 which is parallel to the major or lateral edges of osteotomy guide 12.

Slot 34 extends at an angle of one-half alpha (a/2) with respect to an imaginary line 38 which is showed to be perpendicular to both lines 36 and the major or lateral edges of osteotomy guide 12. Like recess 14, slot 34 terminates in an aperture 40 which is similar in side and corresponds in location to aperture 15 of drill jig 10.

Use Of The Depicted Embodiment

While the use of drill jig 10 and osteotomy guide 12 will be described in the context of a crucial tibial cuneiform osteotomy on a dog, it should be appreciated that the apparatus may be used in a wide variety of other cuneiform osteotomies. To facilitate this description, FIGS. 4–8 depict in a schematic and simplified manner, tibia 40, femur 42 and patella 44 of a dog.

Figure 6:
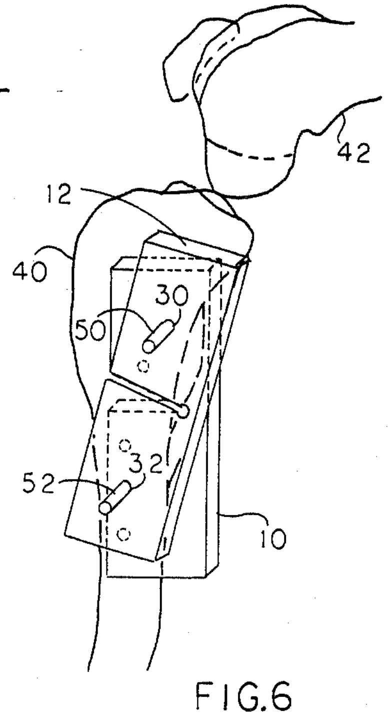
FIG. 6. is a perspective view corresponding to those of FIGS. 4 and 5, showing the osteotomy guide in a second angular position, in which a second bone cut would be taken.
Figure 7:
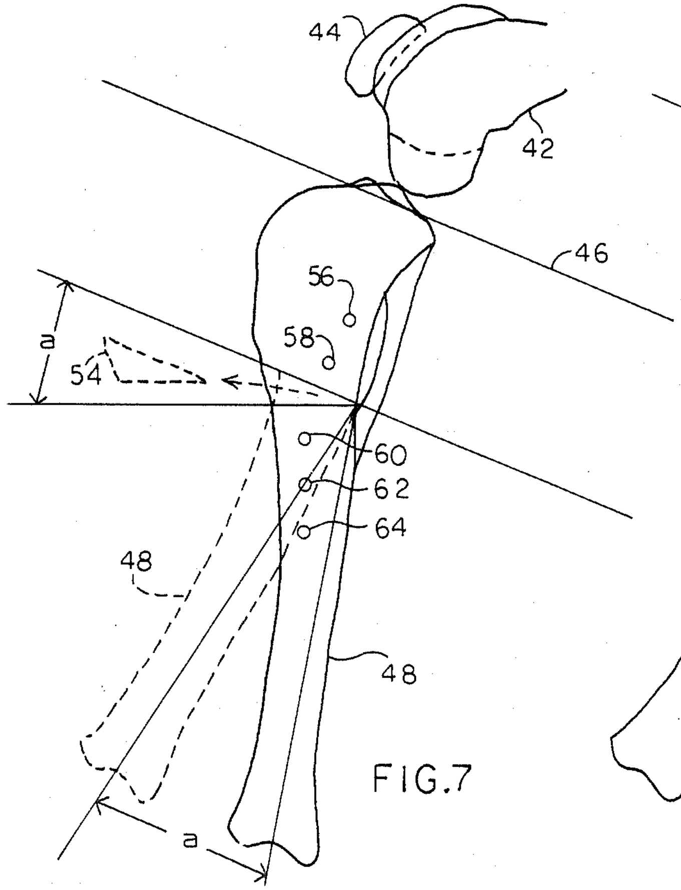
FIG. 7. is a schematic side elevation view of the canine tibia and tibial-femur joint, showing the bone wedge being removed therefrom.

Reference should be made to FIG. 7, to understand the purpose of the cranial tibial cuneiform osteotomy. Line 46 indicates the tibial plane upon which femur 42 rests. Because the tibial plane is inclined with respect to the horizontal, an anterior or cranial force, i.e., to the left as indicated in FIGS. 4–8, is exerted on tibia 40. This so-called cranial tibial thrust is opposed by the cranial cruciate ligament and contributes to the ligament's rupture and prevents or dramatically slows its healing. Therefore, the purpose of the cranial tibial cuneiform osteotomy is to realign the tibia so that forces exerted by femur 42 are absorbed in compression by tibia 40. By realigning the distal portion 48 of tibia 40 by an angle equal to alpha, this object may be achieved. Such realignment is shown in phantom FIG. 7.

Figure 4:
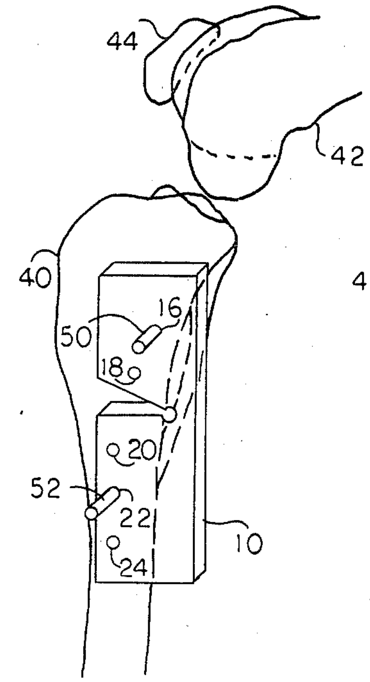
FIG. 4. is a perspective view showing the drill jig depicted in FIGS. 1 and 2, as it would be disposed over the proximal one-third of a canine tibia to a cranial tibial cuneiform osteotomy.

FIG. 4 depicts jig 10 being positioned on and mounted to the proximal one-third of tibia 40. More precisely, drill jig 10 is positioned on the medial side of tibia 40 in the sagittal plane so that the bone wedge to be removed is just distal to the tibial crest. A pair of drill bits 50 and 52, are drilled into tibia 40 through jig bores 16 and 22, and are left in place. Drill bits 50 and 52 are sufficiently long that both drill jig 10 and osteotomy guide 12 may be aligned using the drill bits; that is, the portion of the drill bits extending outwardly from tibia 40 should be substantially greater than the thickness of drill jig 10 and preferably is longer than the combined thickness of drill jig 10 and osteotomy guide 12. Other holes are then drilled in tibia 40 through bores 18, 20, and 24 using a similar drill bit (not shown) but that drill bit is removed.

Figure 5:
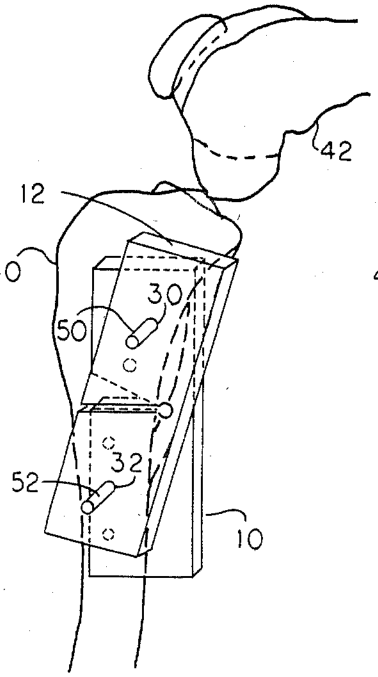
FIG. 5. is a perspective view corresponding to that of FIG. 4, showing the osteotomy guide of FIGS. 1–3, disposed in a first angular position over the drill jig, in which position a first bone cut would be taken.

Osteotomy guide 12 is then placed over drill jig 10 so that drill bits 50 and 52 pass through guide bores 30 and 32, as shown in FIG. 5. This places angular slot 34 of osteotomy guide 12 in a first angular position so that the surgeon may make his first cut in tibia 40 using an osteometric saw (not shown). The walls *34a* and *34b* of angular slot 34 and walls *14a* and *14b* of recess 14 provide a guide for the surgeon during this cutting operation. The relative width of tibia 40 and the length of slot 34 will normally cause entire severance of the tibia, although it is common that the maniscus of the bone and the ligaments and muscles will hold the tibia in place.

Once this first cut has been effected, osteotomy guide 12 is lifted off drill bits 50 and 52 and is turned over end over end and replaced over the drill bits 10 with slot 34 taking a second angular position as shown in FIG. 6. A second cut is then taken, again using walls *34a*, *34b* of slot 34 and walls *14a* and *14b* of recess 14 as a guide. The presence of apertures 35 and 15 in osteotomy guide 12 and drill jig 10, respectively, will normally cause clean removal of a bone wedge, shown schematically at 54. As noted above, however, it is possible that the maniscus, ligaments and muscles will still hold the tibia together. These can be severed using conventional surgical techniques. Without apertures 35 and 15, it is possible that a certain amount of bone would remain adjacent the intersection of the two cuts, and would cause problems in removing bone wedge 54.

Once the two cuts have been effected, guide 12, jig 10 and drill bits 50 and 52 are removed. Bone wedge 54 may then be pulled away and the distal portion 48 of tibia 40 is shifted to the position indicated in phantom in FIG. 7. Holes 56, 58, 60, 62, and 64, which previously had been drilled through jig bores 16, 18, 20, 22, and 24, are then tapped, and an osteometric compression plate 66 is mounted onto the tibia. Plate 66 is screwed into place through holes 56, 58, 60, 62, and 64. To prevent infection, the area is then typically irrigated with a neomycin, bacitracin, and polymixin antibiotic solution.

Figure 8:
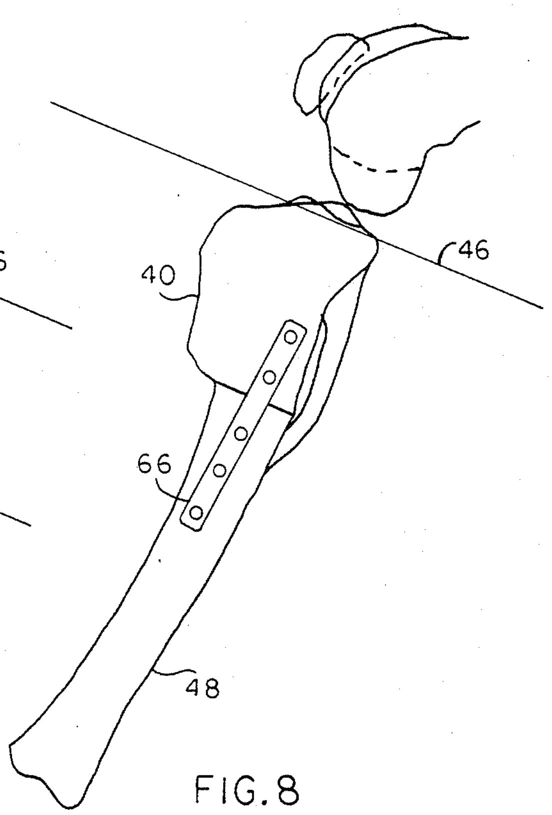
FIG. 8. is a schematic side elevation view corresponding that the of FIG. 7, except that the tibia is shown rejoined with an osteopathic compression plate mounted to hold the bone in position for rejoinder.

With the distal one-third 48 of tibia 40 in its new position depicted in FIG. 8, it can be seen that the tibial plane line 46 is generally perpendicular to the longitudinal axis of the distal one-third of the tibia. This prevents or at least minimizes the cranial tibial thrust described above and permits unstressed healing of the cranial cruciate ligament.

Having neutralized cranial tibial thrust, it is common to perform supplemental techniques to accommodate for the reconfiguration of the tibia. The technique most commonly used is the lateral advancement of the biceps femoris muscle and the medial advancement of the gracilis and semitendinosus. It should be understood, however, that these last-mentioned procedures are optional and may be dispensed with in some cases.

Other changes and modifications to the preferred embodiment described herein will be apparent to those skilled in the art. Such changes and modifications can be made without departing from the spirit and scope of the present invention and without diminishing its attendant advantages. It is therefore intended that such changes and modifications be covered by the following claims.

It is claimed and desired to secure by Letters Patent:

1. An apparatus for performing cuneiform osteotomy comprising:

a jig having first and second faces which terminate in edges and which define a recess extending therethrough and intersecting an edge thereof, said jig further defining a pair of jig bores extending therethrough in a direction substantially perpendicular to said first jig face, one of each of said jig bores being disposed to each side of said recess, said jig bores each being adapted to properly position a drill bit extending therethrough and into the bone against which said second jig face is to be disposed and to which the osteotomy is being performed; and an osteotomy guide having first and second substantially parallel faces which complement said first jig face and which terminate in edges, said guide defining a pair of guide bores extending therethrough in a direction substantially perpendicular to said guide faces, said guide bores being spaced from each other a distance equal to the spacing of said jig bores so that each of said guide bores is adapted to receive one of the drill bits to permit relative alignment of said jig and said guide with respect to each other and to the bone, said guide further defining a slot extending therethrough across less than the entire width of said guide and intersecting an edge thereof, said slot extending at an oblique angle with respect to a line drawn between said guide bores, whereby said guide may be mounted to said jig with either of said guide faces disposed against said first jig face permitting said guide slot to be disposed in a first and then a second angular position with respect to the bone to facilitate cutting the bone in first and second cuts to cut a bone wedge of an angle alpha which is equal to the difference between said first and second angular positions of said slot.

2. The apparatus of claim 1, wherein said jig recess is V-shaped, having edges which conform to said first and second angular positions of said slot, whereby said jig provides guidance for a cutting implement to effect the cutting.

3. The apparatus of claim 1, wherein said jig further defines a plurality of other jig bores extending through said jig in a direction substantially perpendicular to said first jig face, at least one of said other jig bores being disposed on each side of said recess such that said bores are aligned along a pair of lines which intersect at the alpha angle, whereby said bores may be used to drill holes into the bone so that when the bone wedge is removed leaving a pair of bone faces, displacement of the bone to cause the bone faces to abut also causes the drilled holes to align, thereby facilitating the mounting of an osteopathic compression plate.

4. An apparatus for use in performing a cranial tibial cuneiform osteotomy on a dog, comprising:

a jig having first and second faces which terminate in lateral and end edges and which define a recess extending therethrough and intersecting a lateral edge thereof, said jig further defining a pair of jig bores extending therethrough in a direction substantially perpendicular to said first jig face, one of each of said jig bores being disposed to each side of said recess, said jig bores each being adapted to facilitate removable positioning of a pin extending therethrough and into the tibia;

an osteotomy guide having first and second substantially parallel faces which complement said first jig face and which terminate in lateral and end edges, said guide defining a pair of guide bores extending therethrough in a direction substantially perpendicular to said guide faces, said guide bores being spaced from each other a distance equal to the spacing of said jig bores so that each of said guide bores is adapted to receive one of the pins to permit relative alignment of said jig and said guide with respect to each other and to the bone, said guide further defining a slot extending therethrough across less than the entire width of said guide and intersecting a lateral edge thereof, said slot having an open and a closed end and extending at an oblique angle with respect to a line drawn between said guide bores, whereby said guide may be mounted to said jig with either of said guide faces disposed against said first jig face, permitting said guide slot to be disposed in a first and then a second angular position with respect to the tibia to facilitate cutting the tibia in first and second cuts to excise a bone wedge of an angle alpha which is equal to the difference between said first and second angular positions of said slot.

5. The apparatus of claim 4, wherein said jig further defines a plurality of other jig bores extending through said jig in a direction substantially perpendicular to said first jig face, at least one of said other jig bores being disposed on each side of said recess such that said bores are aligned along a pair of lines which intersect at the alpha angle, whereby said bores maybe used to drill holes into the tibia so that when the bone wedge is removed leaving a pair of bone faces, displacement of the tibia to cause the bone faces to abut also causes the drilled holes to align, thereby facilitating the mounting of a osteopathic compression plate.

6. The apparatus of claim 4, wherein said jig recess is V-shaped, having edges which conform to said first and second angular positions of said slot, whereby said jig provides guidance for a cutting implement to effect the cutting.

7. The apparatus of claim 6, wherein a line bisecting said V-shaped recess bisects the angle formed by said pair of intersecting lines.

8. The apparatus of claim 6, wherein said notch subtends an angle of approximately 22.5°.

9. The apparatus of claim 4, wherein said jig faces are substantially planar and parallel and said guide faces are substantially planar and parallel.

10. The apparatus of claim 9, wherein said jig and said guide define a continuous hole extending therethrough adjacent said recess and adjacent said closed end of said slot.

11. A method of performing a cranial tibial cuneiform osteotomy, comprising:

placing, on an exposed medial side of the tibia, a drill alignment jig having first and second faces which terminate in lateral and end edges and which define a recess extending therethrough and intersecting a lateral edge thereof, the jig further defining at least two pairs of jig alignment bores extending through the jig in a direction substantially perpendicular to the first jig face, the two pairs being disposed on opposite sides of the recess toward said end edges such that each pair of jig bores is aligned along a different line, the two lines intersecting at an angle alpha, said placing causing the second jig face to be positioned against the tibia with one end edge being disposed proximally and the other distally;

drilling a proximal hole in the tibia with a drill bit passing through one of the proximally-disposed jig bores, and leaving the drill bit in place;

drilling a distal hole in the tibia with a drill bit passing through one of the distally-disposed jig bores, and leaving the drill bit in place;

drilling additional holes in the tibia with a drill bit passing through the jig's remaining bores;

placing, over the jig, an osteotomy guide having first and second substantially parallel faces which complement the first jig face and which terminate in lateral and end edges, the guide defining a pair of guide bores extending therethrough in a direction substantially perpendicular to the guide faces, the guide bores being spaced from each other a distance equal to the spacing of the jig bores, the guide further defining a slot extending therethrough across less than the entire width of the guide and intersecting a lateral edge thereof, the slot extending at an oblique angle with respect to a line drawn between the guide bores, said placing causing the previously-placed drill bits to extend through the guide bores and causing the first guide face to be positioned against the first jig face;

making a first osteotomy cut in the tibia with an osteotomy saw extending through the guide slot;

turning the guide end over end and placing the second guide face against the first jig face, with the guide bores receiving the previously-placed drill bits;

making a second osteotomy cut in the tibia with an osteotomy saw extending through the guide slot;

removing the guide, jig and drill bits;

removing the bone portion excised by the cuts; and drawing together and securing the separated portions of the tibia with interfragmentary compression.

12. The method of claim 11, wherein the first and second osteotomy cuts are made at an angle of approximately 22.5° with respect to each other.

13. The method of claim 11, wherein said interfragmentary compression is applied by placing a compression plate adjacent the first and second osteotomy cuts, and securing the compression plate to the tibia with screws extending into the holes drilled in the tibia.

* * * * *